(12) United States Patent
Bruna et al.

(10) Patent No.: US 7,829,122 B2
(45) Date of Patent: Nov. 9, 2010

(54) MICROGRANULES BASED ON ACTIVE PRINCIPLE AND METHOD FOR MAKING SAME

(75) Inventors: Etienne Bruna, Jouy (FR); Edouard Gendrot, Garnay (FR); Gérard Cousin, Villemieux (FR)

(73) Assignee: Ethypharm, Houdan (FR)

( * ) Notice: Subject to any disclaimer, the term of this patent is extended or adjusted under 35 U.S.C. 154(b) by 1258 days.

(21) Appl. No.: 10/416,848

(22) PCT Filed: Nov. 15, 2001

(86) PCT No.: PCT/FR01/03584

§ 371 (c)(1),
(2), (4) Date: May 16, 2003

(87) PCT Pub. No.: WO02/39981

PCT Pub. Date: May 23, 2002

(65) Prior Publication Data

US 2004/0101568 A1    May 27, 2004

(30) Foreign Application Priority Data

Nov. 16, 2000 (FR) .................................. 00 14803

(51) Int. Cl.
*A61K 9/16* (2006.01)
*A61K 9/14* (2006.01)

(52) U.S. Cl. ...................................... 424/490; 424/489

(58) Field of Classification Search ................. 424/400, 424/451, 464, 489, 490, 493, 497
See application file for complete search history.

(56) References Cited

U.S. PATENT DOCUMENTS

| | | | |
|---|---|---|---|
| 3,558,768 A * | 1/1971 | Klippel ....................... 424/494 |
| 4,248,858 A * | 2/1981 | Guley et al. .................. 424/493 |
| 4,853,229 A * | 8/1989 | Theeuwes .................... 424/455 |
| 4,892,740 A * | 1/1990 | Takasima et al. ............. 424/474 |
| 4,957,746 A   | 9/1990 | Valducci |
| 5,026,560 A * | 6/1991 | Makino et al. ............... 424/494 |
| 5,344,657 A * | 9/1994 | Desmolin .................... 424/458 |
| 5,476,667 A   | 12/1995 | Kristensen et al. |
| 5,837,292 A * | 11/1998 | Dijkgraaf et al. ............. 424/494 |

FOREIGN PATENT DOCUMENTS

| | | |
|---|---|---|
| EP | 91102524.5 | 8/1991 |
| FR | 79 00916 | 1/1979 |
| WO | WO/95/22319 | 8/1995 |

* cited by examiner

*Primary Examiner*—Humera N Sheikh
(74) *Attorney, Agent, or Firm*—Heslin Rothenberg Farley & Mesiti P.C.; Andrew K. Gonsalves

(57) ABSTRACT

The invention concerns a microgranule consisting of a core coated with at least a coating layer, said coated core comprising at least an active principle. The invention is characterised in that the core and said coating layer contain each between 80 and 95 wt. % of active principle, the complement to 100% consisting of at least a binding agent, and the coated core has a substantially spherical shape. The invention also concerns the method for making such microgranules.

7 Claims, No Drawings

MICROGRANULES BASED ON ACTIVE PRINCIPLE AND METHOD FOR MAKING SAME

This application claims priority to PCT Application No. PCT/FR01/03584 filed on Nov. 15, 2001, which was published as WO 02/39981 on May 23, 2002. The application also claims priority to French Application No. 00.14803 filed on Nov. 16, 2000.

TECHNICAL FIELD OF THE INVENTION

The invention relates to a microgranule consisting of a coated core comprising at least one active principle. It also relates to method for making said microgranule and to the pharmaceutical compositions containing a plurality of said microgranule.

BACKGROUND

The document WO 95/22319 describes a method for making by extrusion/spheronization fine particles based on an active principle. The fine particles obtained have a size of between 50 µm and 1 mm. In particular, the examples describe particles having a size equal to 300 µm, comprising up to 72% of active principle in the presence of at least three excipients including in particular an extrusion agent. In addition, these same examples and in particular formula 1 c shows that this method does not make it possible to obtain fine particles of this order of size with a high concentration of active principle, equal to 95%. Finally, the fine particles obtained at the end of the method have a surface which is too irregular to allow subsequent satisfactory treatment, the coating designed to mask the taste of the active principle requiring, for example, a high level of coating.

The document EP-A-443572 describes a coating composition which can be applied in various forms and in particular microgranules designated here by the expression "fine granules". It is indicated that at least 75% of the population of microgranules have a size of between 1 and 500 µm. No information is given relating to the concentration of active principle in the microgranule.

The document FR-A-2 419 722 describes microgranules of active principle and in particular of ferritin and their method of preparation. These microgranules consist of a core comprising a first coating obtained by spraying an aqueous suspension of active principle, the cohesion of said first coating with the core being brought about by uniform dispersion, between each spraying step, of small quantities of talc (see in particular page 7, example 3). The core thus coated has, in addition, a second coating, whose nature depends on the characteristics of release of the desired active principle. In practice, the core itself can have two different forms. Thus, in a first embodiment, the core consists exclusively of inert material, for example of the sucrose type. In a second embodiment, (example 3), the core exists in the form of a granule based on a binder (for example starch) and an active principle in ratios of 50/50.

The method of manufacture and the microgranule thus obtained exhibit a number of disadvantages. As regards first of all the method of manufacture, it requires at least four steps, which are the manufacture of the core, and then, alternatively, the application of the first coating, and of the talc dispersion and finally the application of the second coating. Such a method is particularly long and cannot be performed continuously. In addition, the cohesion of the first coating onto the core is not always homogenous, leading to coated cores having an irregular surface and thereby increasing the quantity of material necessary for the second coating. As regards the microgranule as such, it is indicated that the core before coating has a size of between 0.3 and 0.5 millimeters (see examples) for a concentration of active principle representing only 50% of the mass of the core.

Accordingly, the first problem which the invention proposes to solve is to provide microgranules whose core, before coating of the functional layer(s) conferring on the microgranule the desired characteristics of release of the active principle and/or of masking the taste, is as concentrated as possible in active principle.

The second problem which the invention proposes to solve is to provide a microgranule whose nucleus, before coating the functional layer(s), is appreciably spherical so as to reduce its specific surface and thus reduce the quantity of material necessary for subsequent coating.

The third problem which the invention proposes to solve is to provide a microgranule whose nucleus, before coating the functional layer(s), has a size which is as small as possible, advantageously a median size of less than 500 µm.

SUMMARY OF THE INVENTION

The subject of the invention is therefore a microgranule consisting of a core coated with at least one coating layer, said coated core comprising at least one active principle.

This microgranule is characterized in that the core and said coating layer each contain between 80 and 95% by weight of active principle, the balance for 100% consisting of at least one binder, and in that the coated core has a substantially spherical shape.

Below an active principle concentration of 80%, the microgranule titer is not sufficient and the proportion of binder is too high, leading to the size of the microgranule being increased. For a concentration greater than 95%, the cohesion between the particles of active principle is not satisfactory because of the extremely low proportion of binder.

In a preferred embodiment, the core and the coating layer each contain between about 85 and 93%, advantageously 90% by weight of active principle.

In an advantageous embodiment, the balance for 100% by weight of the core and of the coating layer consists exclusively of a binder.

The choice of "binder" will be determined as a function not only of its capacity to bind the particles of active principle to each other in the coated core, but also of the desired functional characteristics of the coated core, whether in the presence or in the absence of subsequent functional coating. The expression "functional characteristics" denotes in particular, but without limitation, the properties of masking of taste and/or of release (modified or otherwise) of the active principle.

These functional characteristics depend on: 1) the physicochemical characteristics of the binder used (solubility, permeability, glass transition temperature, and the like); and 2) on the nature of the active principle (solubility, bitterness, and the like).

In other words, before any subsequent functional coating, the microgranule of the invention already has specific characteristics thus making it possible to reduce the thickness of the subsequent coating and therefore the size of the final microgranule.

In practice, the binder is chosen from the group comprising ethyl cellulose, hydroxypropyl cellulose (HPC), carboxymethyl cellulose (CMC), hydroxypropyl methyl cellulose (HPMC), acrylic polymers, methacrylic polymers, amoniomethacrylate copolymer, polyacrylate, methacrylic acid copolymer and polyvinylpyrrolidone.

According to another characteristic, the binder contained in the coating layer and that contained in the core may be identical or different.

DETAILED DESCRIPTION

While the making and using of various embodiments of the present invention are discussed in detail below, it should be appreciated that the present invention provides many applicable inventive concepts that may be embodied in a wide variety of specific context. The specific embodiments discussed herein are merely illustrative of specific ways to make and use the invention and do not delimit the scope of the invention.

As already stated, another objective of the invention is to reduce the size of the coated microgranule before coating the optional subsequent functional layer. The high titer of the microgranules of the invention makes it possible to partially fulfill this objective. To further reduce the size of the microgranules, the size of the particles of active principle varies between 10 and 30 µm.

In practice, the size of the coated microgranules of the invention before optional subsequent coating is less than 500 µm, advantageously between 200 and 300 µm.

Of course and as already stated, the coated core constituting the microgranule of the invention may comprise an additional functional coating, in general of polymeric origin, whose nature will depend on the desired characteristics of the final formulation and in particular of masking taste and/or of modified or unmodified release of active principle.

Because of the specific method of production which will be described later, the microgranules of the invention have, in addition, the advantage of being substantially spherical, thus having a reduced specific surface area which makes it possible to coat a subsequent layer of raw material in reduced quantities compared with the known microgranules of the prior art. This subsequent layer preferably comprises a polymer whose application to the microgranules will make it possible to obtain the desired final characteristics.

Moreover, the microgranules of the invention may be used in various galenical forms such as in particular sachets, gelatin capsules, liquid suspensions, suspensions intended for reconstitution immediately before use. They can also enter into the composition of tablets which are orodispersible or not. In this regard, the reduced size of the microgranules of the invention makes it possible to reduce the proportion of compression excipients (for example the diluents) necessary for producing a homogeneous mixture before compression, which makes it possible to have a final form of smaller size and weight compared with known tablets of the same size and to also reduce the compression forces.

In this regard, the invention relates more particularly to fast disintegrating multiparticulate type tablets such as those described by the applicant in the document FR-A-2 679 451, and fast dispersible type tablets comprising the microgranules described above.

The subject of the invention is also the method for making the microgranules described above according to which:
in a first step, a granulation solution comprising at least one binder in a solvent is sprayed onto the individualized particles of active principle maintained in suspension in a fluidized bed until a core is obtained;
and then, in a second step, the core formed is coated by spraying a coating suspension or solution based on particles of active principle and binder, the coated core obtained then having a substantially spherical shape.

In an advantageous embodiment, a step for drying the cores obtained is intercalated between the first and the second step.

According to another characteristic, the method may be performed continuously or batchwise.

Of course, the solvent in which the binder is dissolved will be determined as a function of the actual nature of the binder and will be chosen from aqueous or organic solvents, alone or in combination.

To solve the problem posed of obtaining coated cores whose size is as small as possible, in any case below 500 micrometers, preferably below 350 micrometers, the size of the particles of active principle used in the first step is between 10 and 30 micrometers, advantageously 25 micrometers, while the size of the particles of active principle used in the second step is between 10 and 20 micrometers, advantageously below 15 micrometers.

Of course, such sizes of particles of active principle may be obtained by any methods known to persons skilled in the art, in particular micronization or grinding.

In an advantageous embodiment, the size of the particles of active principle used in the first step is identical to the size of those used in the second step.

To check, during the method of manufacture, the size of the microgranules as a function of the titer of active principle, the active principle/binder ratio is constant during the first and second steps, advantageously equal to 90/10. Consequently, the second step may be stopped as soon as the desired size of the microgranule, below 500 µm, has been reached.

According to another characteristic, in a third step, at least one additional coating solution is sprayed, whose composition is chosen as a function of the characteristics of masking of taste and/or of release of active principle desired.

As already stated, the method of the invention is formed in a fluidized bed, advantageously by a bottom spray technique. The parameters of the fluidized bed (pressure, spraying rate, and the like) do not exhibit particular characteristics and will be adjusted in the customary manner by persons skilled in the art.

The invention and the advantages resulting therefrom will emerge more clearly from the following exemplary embodiments given by way of illustration and without limitation.

EXAMPLE 1

Manufacture of Microgranules of Ibuprofen a) Composition of the Coated Core

| | |
|---|---|
| ibuprofen | 1600 g |
| HPMC 606* | 160 g |

*manufactured by SHIN-ETSU b) Preparation of the Granulating Solutions and Coating Suspension Granulating Solution 40 g of HPMC 606 are introduced into 360 g of purified water, with stirring until complete dissolution of the hydroxymethyl propyl cellulose is obtained.

Coating Suspension 1 200 g of micronized ibuprofen (25µ) and 120 g of HPMC 606 in 3 080 g of purified water are mixed together, with constant stirring until complete dissolution of the hydroxypropyl methyl cellulose is obtained.

c) Manufacture of the Coated Core 400 g of ibuprofen having a particle size equal to 25 micrometers are introduced into a fluidized bed apparatus of the GLATT GPCG 1 type equipped with a Bottom Spray tank, while the active principle is kept at a temperature sufficient to avoid sticking together while the mass is kept moist.

The granulating solution prepared above is then sprayed until a core having a median particle size of about 100 micrometers is obtained.

After drying the core thus formed, the active principle-based coating suspension is continuously sprayed until a granule is obtained which has a median particle size of between 250 and 300 micrometers.

d) Functional Coating

A polymeric dispersion of ethyl cellulose and HPMC and syloid is applied to the coated core in order to mask the taste of the active principle.

EXAMPLE 2

Manufacture of Microgranules of Tinidazole a) Composition of the Coated Core

| tinidazole | 1600 g |
|---|---|
| Eudragit ® E 100 | 160 g | b) Manufacture of the Coated Core

Example 1 is repeated, replacing HPMC with Eudragit® E 100 and purified water with ethanol.

The Eudragit® is chosen as binder, but also for its function as agent masking the taste of the active principle, while allowing its immediate release. This thereby makes it possible to improve the masking of the taste from the granulation step, before the optional functional coating step.

EXAMPLE 3

Manufacture of Microgranules of Doxycyclin a) Composition of the Coated Core

| doxycyclin | 15 kg |
|---|---|
| PVP K90 | 1.5 kg | b) Preparation of the Granulating Solutions and Coating Suspension

Granulating Solution

Preparation of a granulating solution of PVP K90 at 5% (w/w) in ethanol.

Coating Suspension 25 kg of the solution of PVP K90 at 5% in ethanol obtained above are collected and 10 kg of doxycyclin (10µ) in 23.75 kg of ethanol are added thereto.

c) Manufacture of the Coated Core 5 kg of doxycyclin (10µ) are introduced into a fluidized bed apparatus of the GLATT GPCG5 type equipped with a bottom spray tank and a 12" nozzle.

The granulating solution obtained above is then sprayed. After drying the core thus formed, the active principle-based coating suspension is sprayed continuously until a granule having a median particle size of about 257 µm is obtained.

d) Functional Coating

A polymeric solution of Eudragit® E100 (manufactured by Röhm) at 12.5% (w/w) in ethanol is sprayed on the coated cores. The equivalent of 10% (w/w calculated as dry polymer) of the mass of the coated cores is applied for masking taste.

The invention and the advantages resulting therefrom are clearly evident from the description.

The possibility of making coated microgranules whose coated core has a very small size, below 300 micrometers, facilitating the functional coating and subsequent forming, will be noted in particular.

Although this invention has been described with reference to an illustrative embodiment, this description is not intended to limit the scope of the invention. Various modifications and combinations of the illustrative embodiments as well as other embodiments of the invention will be apparent to persons skilled in the art upon reference to the description. It is therefore intended that the appended claims accomplish any such modifications or embodiments.

What is claimed is:

1. A microgranule comprising:
   a core coated with at least one coating layer,
   wherein said core and said at least one coating layer each comprise between 80 and 95% by weight of active principle, and between 5 and 20% by weight of at least one binder,
   wherein the active principle/binder ratio is constant and equal to 90/10, and
   wherein the microgranule has a substantially spherical shape and a size comprising between 200 and 300 µm.

2. The microgranule as claimed in claim 1, characterized in that the balance for 100% by weight of the core and of the coating layer consists exclusively of binder.

3. The microgranule as claimed in claim 1, characterized in that the binder contained in the core and the binder contained in said coating layer are identical.

4. The microgranule as claimed in claim 1, characterized in that the binder contained in the core and the binder contained in said coating layer are different.

5. The microgranule as claimed in claim 1, characterized in that the binder is chosen from the group comprising ethyl cellulose, hydroxypropyl cellulose (HPC), carboxymethyl cellulose (CMC), hydroxypropyl methyl cellulose (HPMC), acrylic polymers, methacrylic polymers, ammonio-methacrylate copolymer, polyacrylate, methacrylic acid copolymer and polyvinylpyrrolidone.

6. The microgranule as claimed in claim 1, characterized in that the size of the particles of active principle varies between 10 and 30 µm.

7. The microgranule as claimed in claim 1, characterized in that the coated core comprises an additional functional layer whose composition is chosen according to the characteristics of masking of taste and/or of release of active principle desired.

* * * * *